United States Patent [19]

Williams et al.

[11] Patent Number: 5,289,817
[45] Date of Patent: Mar. 1, 1994

[54] ENDOSCOPIC SURGICAL RETRACTOR

[75] Inventors: Donald B. Williams, Deerfield; Peter L. Visconti, Chicago, both of Ill.

[73] Assignee: Linvatec Corporation, Largo, Fla.

[21] Appl. No.: 747,574

[22] Filed: Aug. 20, 1991

[51] Int. Cl.$^5$ ............................................. A61B 17/02
[52] U.S. Cl. ........................................ 128/20; 294/97; 606/198
[58] Field of Search ............... 128/20, 4, 3, 5, 17; 606/190, 205, 210, 191, 198; 294/97; 604/104, 105, 106, 107, 108, 109

[56] References Cited

U.S. PATENT DOCUMENTS

| | | | |
|---|---|---|---|
| 2,034,785 | 3/1936 | Wappler | 128/4 |
| 3,132,890 | 5/1964 | Beaudet | 294/97 |
| 3,316,912 | 5/1967 | Whitaker . | |
| 3,871,365 | 3/1975 | Chikama | 128/5 |
| 4,043,323 | 8/1977 | Komiya | 128/4 |
| 4,178,920 | 12/1979 | Cawood, Jr. et al. . | |
| 4,190,042 | 2/1980 | Sinnreich . | |
| 4,357,940 | 11/1982 | Muller | 606/190 |
| 4,393,872 | 7/1983 | Reznik et al. . | |
| 4,517,965 | 5/1985 | Ellison . | |
| 4,598,699 | 7/1986 | Garren et al. | 128/4 |
| 4,608,965 | 9/1986 | Anspach, Jr. et al. | 128/4 |
| 4,838,595 | 6/1989 | Spillar | 294/97 |
| 4,852,550 | 8/1989 | Koller et al. | 128/4 |
| 4,962,770 | 10/1990 | Agee et al. . | |
| 5,100,430 | 3/1992 | Avellanet et al. | 606/205 |

FOREIGN PATENT DOCUMENTS

| | | | |
|---|---|---|---|
| 640126 | 12/1936 | Fed. Rep. of Germany | 604/106 |
| 3641935 | 6/1987 | Fed. Rep. of Germany | 128/4 |
| 157769 | 7/1990 | U.S.S.R. | 128/4 |
| 9218056 | 10/1992 | World Int. Prop. O. | 606/198 |

Primary Examiner—Richard J. Apley
Assistant Examiner—Karen A. Jalbert
Attorney, Agent, or Firm—Gene Warzecha

[57] ABSTRACT

An endoscopic tissue retractor capable of being inserted through an endoscopic tube and subsequently capable of forming a T-shaped bar at its distal end. The legs of the "T" may be aligned with the axis of the tissue retractor for insertion within an endoscopic tube and situated transversely to the longitudinal axis for actual use. In use, the legs extend to diametrically opposed sides of the longitudinal axis of the tissue retractor and are rotatable in a plane passing through the axis of the endoscopic tube. A transversely slidable locking mechanism is provided to lock the components of the tissue retractor in a desired position.

4 Claims, 4 Drawing Sheets

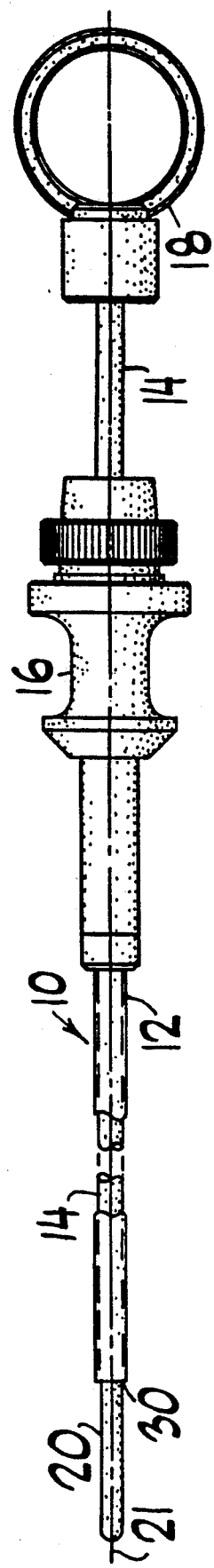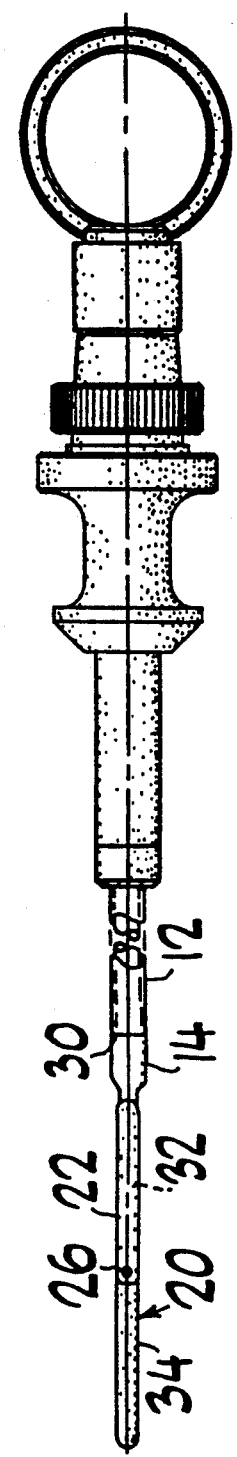

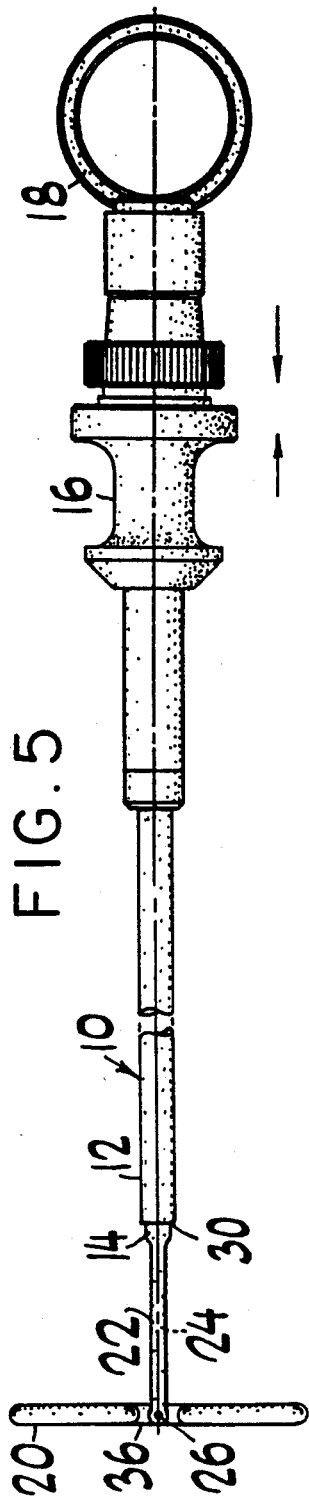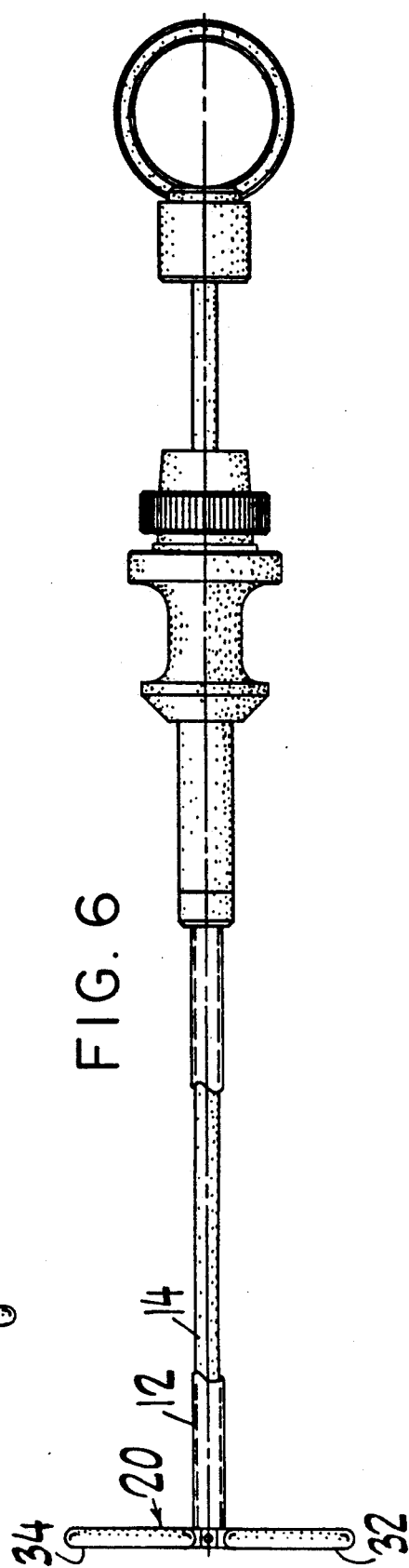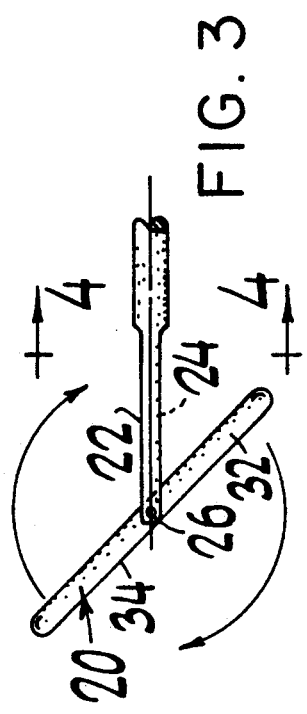

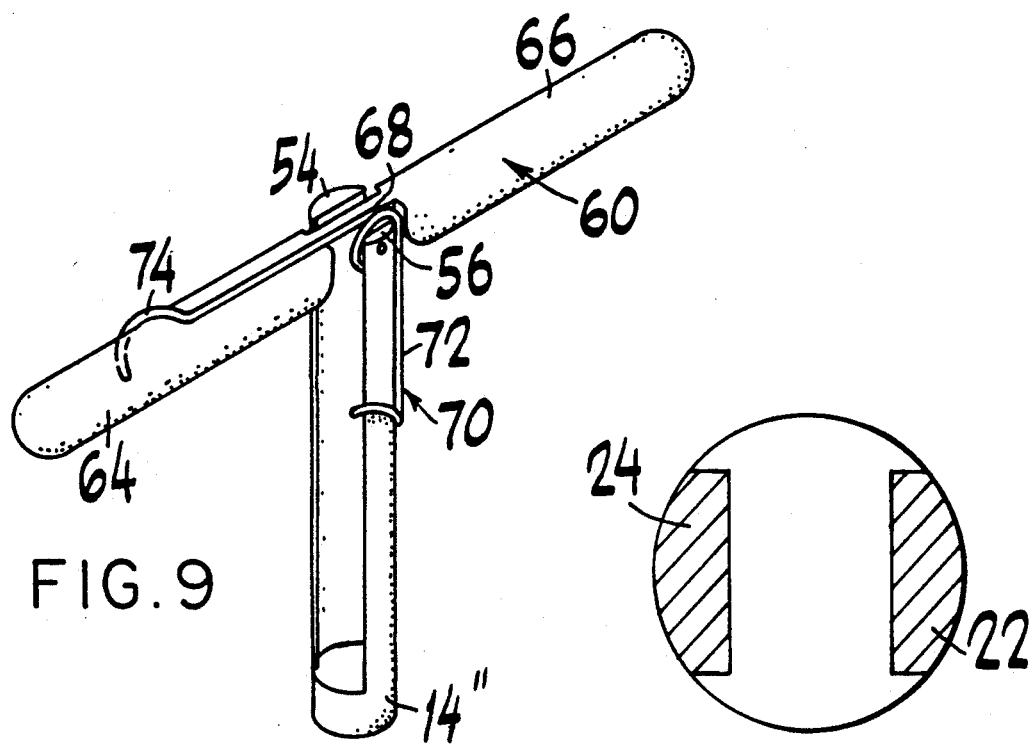
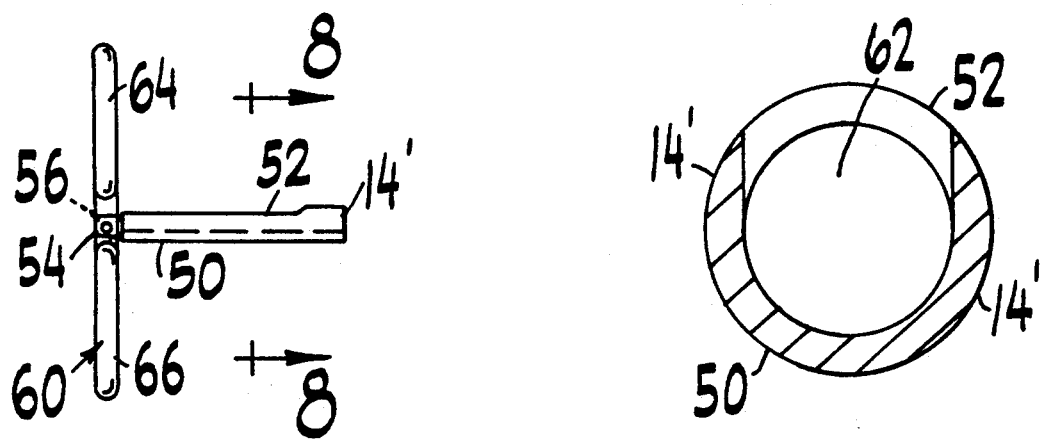

ENDOSCOPIC SURGICAL RETRACTOR

BACKGROUND OF THE INVENTION

1. FIELD OF THE INVENTION

The invention relates generally to the field of surgical instrumentation suitable for endoscopic surgical procedures. More particularly, the invention relates to tissue retracting or manipulating instruments suitable for endoscopic procedures.

2. DESCRIPTION OF THE PRIOR ART

Endoscopic surgical procedures have been used for many years and the popularity of such procedures has recently increased. These procedures employ endoscopes, laparoscopes, cystoscopes and the like, each of which is characterized by an elongated barrel or tube of relatively small diameter which may have a plurality of channels extending between its proximal and distal ends, the latter being inserted into a body cavity. Alternatively, a plurality of single channel tubes may be used. Various elements are inserted into and for illumination of the cavity, another providing visual access into the cavity via fiber optics or the like, while still others provide for insertion and control of specialized surgical tools performing specific functions.

It is particularly important during endoscopic procedures to provide a means for manipulating tissue so that the work area may be properly viewed. The tissue manipulation is generally performed by a tissue retractor and numerous prior art forms of tissue retractors are known.

U.S. Pat. No. 4,393,872 (Reznik et al.) shows one form of tissue retractor utilizing a plurality of resilient fingers which are able to be compressed within the endoscopic tube and, by virtue of their resiliency, spread apart when they are pushed from the tube at the work site. Withdrawing the fingers into the tube causes them to be compressed again in order to enable their withdrawal. These types of retractors are sometimes disadvantageous in that, occasionally, tissue may be caught between the fingers as they are withdrawn.

Another prior art retractor, shown in U.S. Pat. No. 4,190,042, (Sinnreich) comprises a preformed resinous material which is compressible enough to be forced through the endoscopic tube and, upon being pushed from the distal end of the tube, has sufficient memory to produce a relatively rectilinear, scoop-shaped structure. While overcoming some of the disadvantages of other prior art tissue retractors, this device is costly to manufacture and has a greater degree of flexibility than is suitable for certain tissue manipulation.

Some prior art tissue retractors have a push rod extending through the tube which deflects a member at the distal tip of the tube so that the deflected member then extends obliquely relative to the axis of the endoscopic tube. For example, U.S. Pat. No. 4,517,965 (Ellison) shows such a deflectable member as being a retractable barb made of spring steel which, when not biased outwardly by a push rod, is flush with the endoscopic tube.

U.S. Pat. Nos. 3,316,912 (Whitaker), 4,178,920 (Caywood Jr. et al.), and 4,962,770 (Agee et al.) each show an endoscopic type instrument wherein a push rod is pivotably joined at its distal tip to a member which, when the push rod is moved distally, moves into a transverse position relative to the axis of the tube. In each of these instances, the distal member extends only to one side of the endoscopic tube and is, therefore, somewhat limited in its usefulness as a tissue retractor in certain situations.

Several prior art devices are known which have tissue retracting members extending to either side of an endoscopic tube. For example, U.S. Pat. No. 4,608,965 (Anspach Jr. et al.) discloses a "molly bolt" type of structure wherein an outer sheath is provided with a plurality of axially extending flexible tabs circumferentially arranged at its distal tip, the distal end of the tabs being secured to a slidable inner shaft. Retracting the inner shaft relative to the outer shaft causes the ends of the flexible tabs to come together thereby forcing the center of the tabs radially outwardly. This type of arrangement is relatively costly and complex and, because of the necessity for making the tabs resilient, results in a weak device unsuitable in certain situations.

It is an object of this invention to provide a tissue retracting device suitable for endoscopic applications.

It is yet another object of this invention to provide a tissue retracting device suitable for endoscopic application while also being stronger than known tissue retractors and extending transversely to the longitudinal axis of the endoscopic tube.

SUMMARY OF THE INVENTION

These and other objects of the invention are achieved by the preferred embodiment disclosed herein which is a tissue retractor comprising an outer tube having a proximal end, a distal end and a first gripping means at the proximal end thereof. The retractor has an inner rod having a proximal end and a distal end, the inner rod extending through the tube and having a second gripping means at the proximal end thereof, the first and second gripping means adapted for enabling movement of the outer tube and the inner rod relative to each other. A bar is pivotably mounted at the distal end of the rod and rotatable in an axial plane whereby the bar may be alternatively axially aligned with the outer tube or rotated about its pivot point, when the inner rod is extended from the tube a predetermined distance, into a position transverse to the axis of the tube.

The invention also comprises a unique locking mechanism having a transversely slidable apertured bar which is movable between one position where the inner rod is longitudinally slidable and another position where the bar prevents the rod from moving longitudinally.

BRIEF DESCRIPTION OF THE DRAWINGS

FIG. 1 shows a side elevational view of a tissue retractor constructed in accordance with the principles of this invention.

FIG. 2 shows the retractor of FIG. 1 as it may appear during extension of the tissue retractor.

FIG. 3 shows the distal tip of the retractor of FIGS. 1 and 2 during the rotation of a portion of the distal tip.

FIG. 4 is a cross-sectional view of FIG. 3 taken along the line 4—4.

FIG. 5 shows a side elevational view of the tissue retractor of FIG. 1 in an extended position.

FIG. 6 shows a side elevational view of the tissue retractor of FIG. 1 in a normally operating position.

FIG. 7 shows the distal tip of an alternate embodiment of the tissue retractor.

FIG. 8 is a cross-sectional view of FIG. 7 taken along the line 8—8.

FIG. 9 shows a perspective view of an alternate embodiment of the distal tip of the tissue retractor of FIG. 7.

DESCRIPTION OF THE PREFERRED EMBODIMENT

Figure 10:
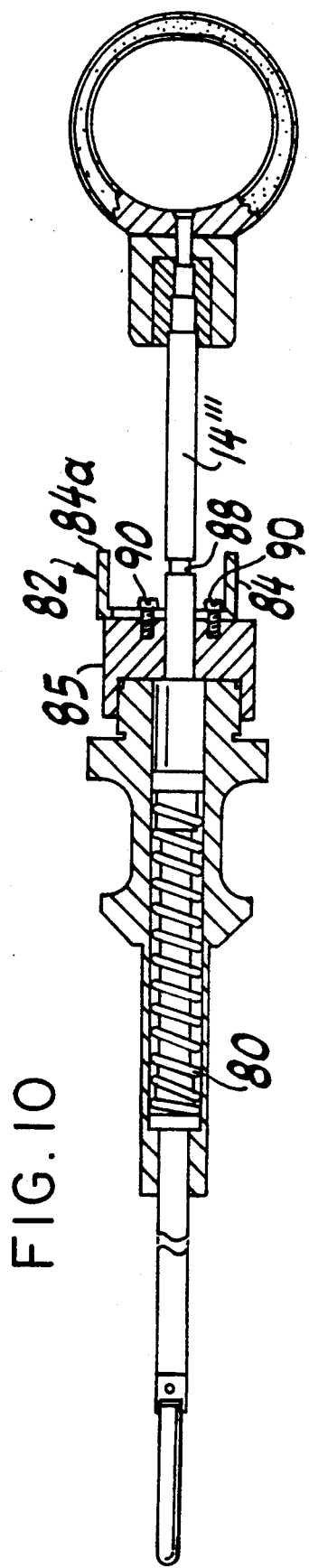
FIG. 10 shows a cross-sectional view of an alternate embodiment of the invention.

Referring to the drawings there is shown a tissue retractor 10 comprising an outer barrel or sleeve 12 and an inner shaft 14 which is longitudinally slidable within outer shaft 12. Outer shaft 12 is provided at its proximal end with a finger grip 16 and inner shaft 14 is provided at its proximal end with a thumb/finger ring 18. It will be understood that movement of the finger grip 16 and thumb ring 18 relative to each other will cause relative movement of shaft 14 and sleeve 12 in a conventional manner.

Outer sleeve 12 has an outer diameter sufficient to fit within an endoscopic tube (not shown). Tissue retractor 10 is insertable into an endoscopic tube in the configuration shown in FIG. 1 wherein the tissue retracting member 20 is in the form of a T-bar, the legs of which are aligned with the longitudinal axis 21 of the tissue retractor. The stem of the T-bar is actually the distal tip of shaft 14. In the embodiment shown in FIGS. 2, 3 and 4 the distal tip of shaft 14 is provided with a pair of parallel arms 22 and 24 aligned with axis 21, the distal tips of the arms being apertured to receive a hinge pin 26. Tissue retracting member 20 is pivotably mounted at the distal tip of inner shaft 14 by engaging a central aperture of member 20 (not shown) with hinge pin 26. It will be understood that tissue retracting member 20 will consequently be free to rotate 360° about the distal tip of inner shaft 14. In one orientation, tissue retracting member 20 will be aligned with the longitudinal axis of tissue retractor 10 (as shown in FIG. 1).

Once the tissue retractor is sufficiently inserted through an endoscopic tube, thumb ring 18 may be moved distally relative to grip 16 to extend the tissue retracting member 20 beyond the distal tip 30 of outer shaft 12 to the position shown in FIG. 2. When the proximal leg 32 of tissue retracting member 20 is clear of the end 30 of outer sleeve 12, the distal leg 34 of tissue retracting member 20 may be moved by pushing against a selected spot at the work site to rotate tissue retracting member 20 as shown in FIG. 3. Movement of thumb ring 18 proximally relative to finger grip 16 (for example by a spring loaded mechanism 80 within grip 16, best seen in FIG. 10) will then cause legs 32 and 34 of tissue retracting member 20 to be positioned transversely relative to longitudinal axis 21 as shown in FIGS. 5 and 6.

Figure 11:
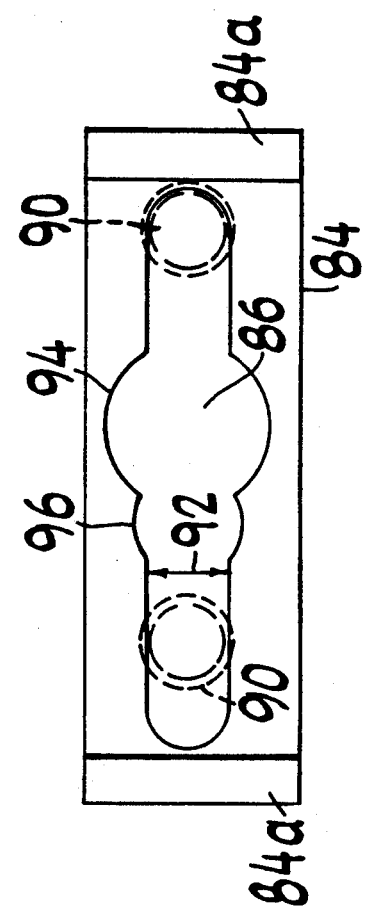
FIG. 11 shows a plan view of a portion of a locking mechanism used in the embodiment of FIG. 10.

In the preferred embodiment both outer sleeve 12 and tissue retracting member 20 may be made of either sterilizable (reusable) metallic materials or disposable materials of relatively hard plastic. The abutting connection between tissue retracting member 20 and distal tip 30 (as shown in FIG. 6) aided by the spring compression provided by the aforementioned spring mechanism 80 produces a solid connection which makes the device suitable for moving firm tissue. An alternative or additional locking mechanism 82 is also shown in FIGS. 10 and 11. Lock 82 includes a flat bar 84 having a uniquely shaped aperture 86 intended to cooperate with groove 88 in inner shaft 14'''.

The operation of the instrument shown in FIG. 10 is the same as that shown in FIGS. 1, 2, 5 and 6 except for the locking mechanism. Bar 84 is slidingly attached to cap 85 by screws 90, the heads of which are larger than the width 92 of the ends of aperture 86. The central portion of aperture 86 is formed of two circular apertures 94 and 96, the latter sized to fit within groove 88 and the former sized to allow longitudinal sliding motion of shaft 14'''. Finger tabs 84a extending away from bar 84 allow it to be pushed transversely to either lock or unlock the inner shaft. It will be understood that locking mechanism 82 may be incorporated into instruments other than tissue retractors.

Other embodiments of the distal tip of the invention are shown in FIGS. 7, 8 and 9. The distal tip of these embodiments are designated 14' and 14", the remaining (i.e. proximal) parts of these embodiments are the same as FIG. 1. Referring to FIG. 7, the distal tip of inner shaft 14' is produced in the form of a channel 50 having one open side 52 and a pair of short walls 54 and 56 extending from the distal end of channel tip 50. Walls 54 and 56 provide a means for supporting the pivot pin (not shown) by means of which member 60 is supported at the distal end of shaft 14a. The length and width of channel 62 are sufficient to accommodate leg 64 of member 60. It will be understood that the embodiment shown in FIGS. 7, 8 and 9 is capable of rotating only 90° from a position in which leg 64 is aligned with the axis of shaft 14'(and 14") to the position shown in FIGS. 7 and 9.

The embodiment of FIG. 9 differs from FIGS. 7 and 8 in the use of a return spring 70 having a leg 72 adapted to press against the distal tip of shaft 14" and a leg 74 adapted to press against leg 64 of member 60. The spring is provided to bias member 60 into a closed position. With the use of spring 70, member 60 will tend to stay aligned with shaft 14" even when it is extended from the outer shaft. Pushing leg 66 against an interior surface at the work site will turn member 60 on its pivot axis and then moving the inner and outer shaft grips 16 and 18 away from each other will cause member 60 to assume the position shown in FIG. 6.

Tissue retracting members 20 and 60 may be formed in a variety of cross-sections. For example, member 60 may be a cylindrical rod wherein the central portion 68 and each leg 64, 66 have the same diameter in the axial plane. Central portion 68 may be narrower in a transverse plane (as shown in FIG. 9). Alternatively, legs 64 and 66 may be made of square cross-section while central portion 36 could be made of a different cross-section.

It will be understood by those skilled in the art that numerous modifications and improvements may be made to the preferred embodiment of the invention described herein without departing from the spirit and scope thereof.

What is claimed is:

1. An endoscopic tissue retractor comprising:
an outer tube having a proximal end, a distal end and a first gripping means at the proximal end thereof;
an inner rod having a proximal end and a distal end, said inner rod extending through said tube and having a second gripping means at the proximal end thereof, said first and second gripping means adapted for enabling movement of said outer tube and said inner rod relative to each other, said inner rod further comprising a pair of spaced longitudinally extending arms secured to the distal end of said inner rod;

a single bar pivotably mounted at its midpoint at the distal end of said spaced arms of said rod and rotatable in an axial plane whereby said bar may be alternatively axially aligned within said outer tube or rotated about its pivot point when said inner rod is extended from said tube a predetermined distance.

2. A locking mechanism in combination with a surgical instrument having an inner rod adapted to be longitudinally slidable within an outer sleeve, the locking mechanism comprising:

a transversely slidable flat bar provided with an aperture having a first enlarged central portion, adapted to receive said inner rod therethrough, and, adjacent thereto, a second enlarged central portion, the latter being smaller than the former;

means for enabling said flat bar to slide transversely to axially align either said first or second enlarged central portion;

an annular groove in the surface of said inner rod to receive said second enlarged central portion.

3. An endoscopic tissue retractor comprising:

an outer tube having a proximal end, a distal end and a first gripping means at the proximal end thereof;

an inner rod having a proximal end and a distal end, said inner rod extending through said tube and having a second gripping means at the proximal end thereof, said first and second gripping means adapted for enabling movement of said outer tube and said inner rod relative to each other;

a bar pivotably mounted at the distal end of said rod and rotatable in an axial plane whereby said bar may be alternatively axially aligned within said outer tube or rotated about its pivot point when said inner rod is extended from said tube a predetermined distance;

a channel formed in the distal end of said inner rod, said channel adapted to receive a portion of said bar when same is aligned with said outer tube.

4. An endoscopic tissue retractor comprising:

an outer tube having a proximal end, a distal end and a first gripping means at the proximal end thereof;

an inner rod having a proximal end and a distal end, said inner rod extending through said tube and having a second gripping means at the proximal end thereof, said first and second gripping means adapted for enabling movement of said outer tube and said inner rod relative to each other;

a bar pivotably mounted at the distal end of said rod and rotatable in an axial plane whereby said bar may be alternatively axially aligned within said outer tube or rotated about its pivot point when said inner rod is extended from said tube a predetermined distance;

a locking mechanism through which said inner rod extends, said locking mechanism comprising:

a transversely slidable flat bar provided with an aperture having a first enlarged central portion adapted to receive said inner rod therethrough, and, adjacent thereto, a second enlarged central portion, the latter being smaller than the former;

means for enabling said flat bar to slide transversely to axially align either said first or second enlarged central portion;

an annular groove in the surface of said inner rod to receive said second enlarged central portion.

* * * * *